United States Patent [19]

Kosak et al.

[11] Patent Number: 5,550,044
[45] Date of Patent: Aug. 27, 1996

[54] PREPARATION OF WAX BEADS CONTAINING A REAGENT USING LIQUID NITROGEN FOR COOLING AND SOLIDIFYING

[76] Inventors: Kenneth M. Kosak; Matthew K. Kosak, both of 3194 S. 4400 West, West Valley City, Utah 84120

[21] Appl. No.: 257,567

[22] Filed: Jun. 10, 1994

Related U.S. Application Data

[63] Continuation-in-part of Ser. No. 936,357, Aug. 27, 1992, Pat. No. 5,413,924, which is a continuation-in-part of Ser. No. 835,758, Feb. 13, 1992, abandoned.

[51] Int. Cl.$^6$ .............. C12N 11/02; C12N 11/08; G01N 33/544; C07K 17/00
[52] U.S. Cl. .............. 435/177; 435/6; 435/7.1; 435/180; 436/535; 530/812; 530/817
[58] Field of Search .............. 435/6, 7.1, 154, 435/178, 180, 12; 436/528, 535; 530/812, 817

[56] References Cited

U.S. PATENT DOCUMENTS

| | | | |
|---|---|---|---|
| 3,868,199 | 2/1975 | Fera | 425/10 |
| 4,384,835 | 5/1983 | Bland | 425/7 |
| 5,106,633 | 4/1992 | Edens et al. | 426/8 |
| 5,130,343 | 7/1992 | Frechet et al. | 521/62 |
| 5,200,236 | 4/1993 | Lang et al. | 427/213 |

*Primary Examiner*—David M. Naff

[57] ABSTRACT

Droplets of molten wax or waxy polymer containing a reagent are dropped onto the surface of liquid nitrogen, the droplets remain on the surface until solidified and the droplets are removed from the surface before they sink into the liquid nitrogen to provide beads containing the reagent. The reagent can be any material that can be entrapped in the beads and does not undergo excessive inactivation when the beads are melted by heating to release the reagent. Examples of reagents are heat resistant enzymes, enzyme substrates, metal salts, oligonucleotides, inclusion compounds, surfactants, emulsifiers, antioxidants, stabilizers, drugs, antibiotics, antibodies and antigens. An apparatus for producing the beads contains a plurality of channels through which liquid nitrogen flows from a reservoir. Each channel passes under a dispenser tip from which droplets are formed and released onto the surface of flowing liquid nitrogen. Liquid nitrogen containing the beads flows from each channel into a pipe and then over a separation sieve. The beads can be used in various in vitro chemical, biochemical and immunological reactions including the PCR, where the reagent is released by heating and melting the beads. The beads have all the combined features for commercial use of: (a) spherical shape, (b) uniform, narrow size range (i.e. 5% or less deviation), (c) free of water contamination, (d) contain an aqueous reagent, and (e) can be produced at high speed (i.e. over 1000 per min.).

17 Claims, 2 Drawing Sheets

PREPARATION OF WAX BEADS CONTAINING A REAGENT USING LIQUID NITROGEN FOR COOLING AND SOLIDIFYING

This application is a continuation-in-part of application Ser. No. 07/936,357, filed Aug. 27, 1992, now U.S. Pat. No. 5,413,924, which is a continuation-in-part of application Ser. No. 07/835,758, filed Feb. 13, 1992, now abandoned.

FIELD OF THE INVENTION

This invention relates to the preparation of beads from drops of fluid material that are exposed to liquid nitrogen. Specifically, it relates to the preparation of wax or waxy polymer beads containing entrapped reagent that can be used in various in vitro chemical, biochemical and immunological reactions where the reagent is released by heating and melting the bead.

RELATED PATENT APPLICATIONS

This is a continuation-in-part application of U.S. patent application Ser. No 07/936,357, filed Aug. 27, 1992, as a C.I.P. of U.S. patent application Ser. No. 07/835,758. Priority for this application is also claimed through U.S. patent Office Disclosure Documents No. 330269, dated May 6, 1993 and No. 342645, dated Nov. 8, 1993.

DESCRIPTION OF THE PRIOR ART

The advantages of dispensing reagents and other substances in premeasured amounts is well known. In the areas of chemistry, biochemistry, molecular biology and especially in clinical testing, the use of premeasured powders, capsules and tablets greatly facilitates the speed and accuracy of routine procedures.

A variety of chemical reactions are improved through the addition of heat. Increased temperature is of particular importance in certain biochemical reactions such as nucleic acid hybridizations where heat is frequently used to increase the specificity of the binding reaction. Elevated temperatures (i.e. 70°–90° C.), are also useful in overcoming problems of secondary RNA structures in the reverse transcriptase reaction (RTR), used to produce complementary DNA (cDNA) from RNA (Biochemistry 30, 7661–7666, 1991). Elevated temperatures are also useful in DNA sequencing procedures.

Heat is employed in nucleic acid amplification using the polymerase chain reaction (PCR). The PCR (U.S. Pat. Nos. 4,683,202 and 4,683,195) employs a heating and cooling cycle to drive the reaction. First, the reaction mixture is heated to, or above, the nucleic acid melting temperature (denaturization), then cooled to allow specific oligonucleotide primers to bind to the sample (annealing), and then heated to optimize the addition of complementary bases to the amplified nucleic acid (extension). Using heat stable, Taq DNA polymerase (U.S. Pat. No. 4,889,818), this cycle of denaturing, annealing and extension is repeated as many times as needed to generate the desired product.

The PCR has become a major tool in molecular biology, and the need for high specificity during amplification is an important problem. One method for increasing PCR specificity is pre-amplification heating. This method has been described by H. A. Erlich, et al, Science 252, 1643–1651 (1991), and R. T. D'Aquila, et al, Nucleic Acids Res. 19, 3749 (1991). It requires exclusion of at least one essential reagent (dNTP's, $Mg^{2+}$, DNA polymerase or primers), from the reaction until it has been heated to the desired annealing temperature. However, the procedure usually requires that the aqueous sample is covered with a vapor barrier such as oil, to reduce evaporation. Or, the container is closed while heating, and reopened for addition of the missing reagent. This procedure is also called HotStart PCR by Perkin Elmer Cetus, Conn.

Wax has become an important material for use in the PCR and in other molecular biology procedures. For instance, Lumitekk, of Salt Lake City, Utah, is presently selling a wax bead with $MgCl_2$ inside (Mg HotBead™), that is released into a PCR reaction when it is melted. Several compositions and methods are disclosed in U.S. patent application Ser. No. 07/936,357, that involve heat-releasable reagents encapsulated in wax or "waxy polymer" beads. The inventors in the copending application are the same as in the instant application.

During the preparation of bead compositions composed of aqueous reagents suspended in wax, we discovered a specific need for quickly solidifying the beads to inhibit separation of the aqueous suspension from the molten wax. And, for PCR applications, we needed wax beads that contained specific, purified reagents and were free of any contaminating materials. Contaminating materials can include any material that will unduly interfere or alter the intended chemical reaction that the bead contents are meant to participate in. For instance, interfering trace metals, proteins, bacteria, viruses, RNAses, and DNAses. Especially for use in the PCR, a single fragment of DNA can ruin the reaction.

In order to use a single bead to initiate a reaction, they must be of uniform size for comparable results between each reaction. We also found that a spherical bead is needed to facilitate manipulation and for dispensing the individual beads. The terms "spherical" bead or "mostly spherical" beads, mean a bead that has curvature on its entire surface, defined in more detail below. A search of the prior art of using wax in biochemical applications showed that it has been either too difficult or expensive to make large spherical wax beads, or there was no motivation for one to address such a specific problem. For instance, Perkin Elmer Cetus now sells a nonspherical wax pellet (Ampliwax™) that is used to make a wax barrier in a PCR reaction tube that separates some of the reagents until the tube is heated to melt the barrier. This approach is disclosed in foreign patent application PCT/US91/01039, filed Feb. 15, 1991.

The wax pellets are made by dispensing molten wax onto a solid moving surface such as a moving belt or drum. The pellets must then be scraped from the surface resulting in a nonspherical pellet with a flattened surface that hinders rolling of the pellet. Also, the rate of production is limited by the rate that the surface can be mechanically moved to carry each pellet away before the next one is dispensed. Since these wax pellets have now been sold for several years, Perkin Elmer apparently found no need for a spherical wax bead that releases reagents to start a reaction when melted.

British Patent No. 1,411,131, a method is described where molten wax is projected upward into a space where an upward moving fluid circulates and cools the wax into particles. And Fera, in U.S. Pat. No. 3,868,199 teaches a method for making wax spheres in the range from about 18 to 80 microns by spraying molten wax upward into a high velocity stream of cold air. These methods have the disadvantage of requiring force to project the wax upward which makes it more difficult to dispense the wax into uniformly sized droplets. Due to their weight, suspension of larger beads in air becomes more difficult, putting a practical upper limit on their size.

Generally, a denser liquid, especially water, is used to make larger beads not easily suspended in air, such as one millimeter diameter or more. Those skilled in the art will appreciate the problems of making spherical wax beads in water. For instance, it is known that dropping large molten wax droplets onto the surface of water causes their deformation, resulting in very low sphericity. One example of making wax beads in water is disclosed by Batchelder, et al, U.S. Pat. No. 2,570,423.

Also, R. P. Bland, in U.S. Pat. No. 4,384,835, describes a method for producing wax beads by releasing discrete droplets of molten wax under the surface of a denser liquid such as water. The method employs releasing molten wax from a heated nozzle at the bottom of a water filled column. The wax droplets solidify into spherical beads as they cool and float up to the surface of the water. One disadvantage of this method is that the polymer used is limited in that it must be less dense than the water in order to float to the top. Also, there is no provision for preparing beads with entrapped reagents such as by mixing an aqueous reagent with the wax during bead making. Perhaps this is true because when the wax is not flowing upward through the nozzle, water can enter the wax reservoir, which would then be mixed with the wax.

D. J. Shimandle in U.S. Pat. No. 5,185,108 teaches a method for making wax microspheres using a "motive liquid" such as pressurized hot water flowing through an eductor into which the molten wax is drawn and then sprayed into a cooler liquid (preferably water), producing wax spheres in the range of 1 to 500 microns diameter.

One problem with using water is that the water must eventually be removed by drying the beads, which may leave a residue and requires additional steps. Also, when wax beads are to be made for use in biochemical tests, and molecular biology, such as PCR, the beads must be free of contaminating materials such as proteins, bacteria, viruses, DNA, RNAses, and DNAses. Also, many enzymatic procedures in biochemistry are inhibited by trace amounts of metals such as Cu and Fe, among others. To avoid these contaminants would then require the use of highly purified, essentially sterile water which can be inconvenient and expensive.

To our knowledge, there has not been a need previously to make large wax beads of one millimeter diameter or more, that have all the combined features of: (a) spherical shape, (b) uniform, narrow size range (i.e. 5% or less deviation), (c) free of water contamination, (d) contain an aqueous reagent, and (e) can be produced at high speed (i.e. over 1000 per min.), for commercial use.

As will become apparent with the disclosures to follow, the instant invention solves these problems with other advantages by producing large beads for use in various biochemical applications including the PCR as well as in other methods such as nucleic acid hybridizations. The instant invention solves these problems without the limitations of a mechanically moving surface or scraper, without the need for water as a vehicle, and without the limitations of projecting wax upward into circulating air or fluid. The methods and reagents disclosed in the references herein are hereby incorporated into this patent application by reference.

SUMMARY OF THE INVENTION

This invention is directed toward the preparation of waxy polymer beads or particles, especially large spherical wax beads that are formed from droplets contacted with liquid nitrogen ($LN_2$). This invention is especially suitable for making mobile, dispensable waxy polymer beads that contain other materials such as any heat-releasable reagent.

Surprisingly, it was found that molten wax does not have to be suspended within a denser fluid such as water, to form a spherical shape. It has been discovered that wax droplets can be dropped onto the surface of liquid nitrogen to form spherical beads. Although denser than $LN_2$, it was surprising that wax droplets remained on the surface of the $LN_2$ while solidifying into a bead. Apparently, they are suspended on a nitrogen vapor layer generated by the heat of the bead in contact with the $LN_2$. Once the beads have cooled sufficiently and generate less vapor, they sink into the $LN_2$.

When under the $LN_2$ surface, wax beads frequently become fractured from the extreme cold and easily disintegrate. However, it was discovered that the beads remain on the $LN_2$ surface about 10 seconds before sinking, which we discovered is sufficient time to remove them from the $LN_2$ and avoid fracture.

The unexpected discovery was also made that, even though $LN_2$ is "similar in appearance to water" (CRC Handbook of Chemistry and Physics, 64th Edition, page B23), dropping molten wax droplets onto the $LN_2$ surface does not cause deformation as water does. In fact, it was interesting to see that wax droplets of 10 or more milligrams could be dropped from 2 or more inches above the $LN_2$ without deformation. Apparently, the low density of the $LN_2$ cushions the fall of the droplets, which penetrate the $LN_2$ surface and rise back to the top as spherical beads. This is a surprising contrast to water which deforms or splatters the droplets from the same height.

Other advantages were also discovered. For instance, $LN_2$ is economical, essentially inert, noncontaminating, nonflammable, and safe to use in a ventilated area. A major advantage over water is that after separating the beads from the $LN_2$ any leftover nitrogen evaporates without any residue. However, it is necessary to use insulated containers and materials that can withstand the extreme change in temperature when exposed to $LN_2$. Generally, such materials as stainless steel (S.S.), aluminum, polystyrene foam (Styrofoam), polyethylene foam, polyurethane foam, polypropylenes, silicon rubbers, polyfluorinated polymers (i.e. Teflon™, E.I. dupont de Nemours), acetal polymers, neoprenes and polybutyls have been found suitable.

DETAILED DESCRIPTION OF THE PREFERRED EMBODIMENTS

For the purposes of this invention, the following definitions are used.

Drop or Droplet

A drop or droplet is defined as a small quantity of fluid material released from an orifice such as a tube, pipe or nozzle by various means.

Fluid Material

Fluid Material is defined as the flowable material to be formed into drops or droplets which are subsequently formed into beads. Said fluid material can be a melted wax or waxy polymer alone or in combination with any of the reagents for entrapment described herein. In some cases, the fluid material can be an aqueous mixture or solution that is fluid at room temperature, and beads are formed by freezing the droplets.

Spherical or Mostly Spherical

A "spherical" bead or "mostly spherical" bead is defined as a bead that has enough curvature on its entire surface, so that when at rest on a flat, level surface, it will roll by the force of gravity when the surface is tilted at an angle of 20 degrees or less.

Liquid Nitrogen

Liquid nitrogen (hereinafter "$LN_2$"), is defined as nitrogen gas that has been condensed to form the liquid state, boiling point −195.8° C.

Entrapment

Entrapment means completely enclosing a substance within an entrapping material to form a barrier between the outside medium and the entrapped substance.

Entrapping Material

An entrapping material is defined in this invention as a wax or wax-like polymer or composition containing a polymer, that is water resistant or water insoluble and is not readily dissolved with acids, bases, enzymes, antibodies or lytic agents. Therefore, there is no dissolution and release of the entrapped substance when held in an aqueous medium below the critical melting temperature of the entrapping material. Also, the entrapping material is for in vitro use and is nonreactive enough that there are no adverse reactions with substances in the surrounding medium.

Heat-Releasable

Heat-releasable refers to a reagent or an entrapping material used in a composition comprising one or more reagents entrapped within an entrapping material that can be melted, dissolved, lysed or dispersed when exposed to the desired critical melting temperature. Preferred critical temperatures are above room temperature especially above 30° C., the upper limit depending on the heat tolerance of the reagents used and the type of reaction employed.

Dispensable Body

A dispensable body is defined as a mostly spherical bead or particle that is mobile in that it can be readily dispersed or dispensed into a medium. Depending on the desired application, the size of the dispensable body may vary. A small dispensable body is defined as a small particle (i.e. less than about one millimeter in diameter), such as a granule, microcapsule, or "microbead", it can be dispensed as a suspension, emulsion, colloid or slurry in a liquid medium or it can be dispensed as a free-flowing powder. A large dispensable body is defined as a larger particle (i.e. greater than one millimeter diameter) it can be dispensed as a bead, pellet or capsule. The large dispensable bodies are preferred because they are more easily used to dispense individual, accurate portions of entrapped reagent.

Reagents for Entrapment

A reagent for entrapment or entrapped reagent is defined as any suitable substance that can be entrapped in a heat-releasable material and subsequently heated without excessive inactivation for release into a reaction. In certain applications, reagents for entrapment can also include any useful enzymes, hormones, proteins, steroids, and other biological materials that are combined with other substances, including water, to make a fluid material that does not include a heat-releasable material. Preferred examples are:

a) Heat Resistant Enzymes: Heat resistant enzymes are a preferred group of reagents for entrapment. For the purposes of this invention, a heat resistant enzyme is defined as any enzyme that retains most of its activity after one hour at 40° C. under optimal conditions. Many such enzymes can be used such as those from thermophilic organisms. For example, various RNA polymerases such as Q beta replicase from bacteriophage, among others, and various enzymes including DNA polymerases from Thermus sp. such as from *Thermus aquaticus* ("Taq"), *Thermus thermophilus* ("Tth"), *Thermus fiavus* ("Tfl"), and *Thermus brokianus.* Also included are enzymes from Thermoccocus sp. such as *Thermococcus litoralis* ("Tli" or "Vent™ New England Biolabs"); from Pyroccocus sp. such as *Pyroccocus furiosus* ("Pfu"); and from Thermotoga sp. such as *Thermotoga maritima* ("Tma"); as well as RNA and DNA ligases such as "ampligase", from Epicentre Technologies, and any "recombinant" enzymes (i.e. rTaq, rTth, rTfl, rTli, and rPfu, among others). Also, any other enzymes from thermophilic microorganisms and invertebrates, including forms produced by recombinant DNA technology. Other enzymes that can be used are reverse transcriptases, restriction endonucleases, kinases, proteases, thioredoxins, nucleases, RNAses, DNAses, phosphatases (i.e. alkaline phosphatases "AP"), peroxidases (i.e. horseradish peroxidase "HRP") and many others. Preferably these enzymes have sufficient thermally stable properties naturally (i.e. by isolation from thermophilic organisms), or by suitable chemical modification, or by genetic engineering.

b) Enzyme Substrates: Another useful group of reagents for entrapment in heat-releasable compositions is any suitable substrate. For example, in the PCR, these include any labeled or unlabeled nucleotides and nucleoside triphosphates (NTP's), any deoxynucleoside triphosphates (dNTP's), any dideoxynucleoside triphosphates (ddNTP's) and ribonucleoside triphosphates. Some examples are; 2'-deoxyadenosine 5'-triphosphate (dATP), 2'-deoxycytidine 5'-triphosphate (dCTP), 2'-deoxyguanosine 5'-triphosphate (dGTP), 2'-deoxythymidine 5'-triphosphate (dTTP), 2'-deoxyuridine 5'-triphosphate (dUTP), 2'-deoxyinosine 5'-triphosphate (dITP), 7-deaza-2"-deoxyguanosine 5'-triphosphate (I-N7-dGTP), among others. Also included are members of this group labeled with radioactive nuclides such as $^3H$, $^{14}C$, $^{32}P$, $^{35}S$, and $^{125}I$, among others.

Also included are various derivatives, analogs and labeled forms of NTP's, dNTP's and ddNTP's, such as biotin labeled, bio-4-dUTP, and bio-11-dUTP, also dNTP's labeled with digoxigenin (DIG-UTP, DIG-dUTP, DIG-ddUTP, Biotechniques 12, 104–113 (1992)), sulfur, cyclodextrins, fluorophores, isotopes, and amino groups such as 5-(3-aminoallyl)-2'-deoxyuridine 5'-triphosphate (AA-dUTP).

c) Phosphorylated Substrates: Another group of reagents for entrapment is any phosphorylated substrate that produces a colored, fluorescent or chemiluminescent product when dephosphorylated, as with AP, such as 5-bromo- 4-chloro-3-indoyl phosphate (BCIP) and nitro blue tetrazolium (NBT); 4-methylumbelliferyl phosphate, and any phosphorylated dioxetanes (3-(2'-spiroadamantanane)- 4-methoxy-4-(3"-phosphoryloxy)phenyl-1,2-dioxetane (AMPPD)) and HMPPD, among others.

d) Oxidase Substrates: Another group of reagents for entrapment is any substrates for peroxidases such as o-phenylenediamine (OPD), 3,3'-diaminobenzidine tetrahydrochloride dihydrate (DAB), and 3,3',5,5'-tetramethylbenzidine (TMB), among others.

e) Metal Salts: Another group of reagents for entrapment is various salts (i.e. chlorides or sulfates), of metals such as Mg, Mn, Fe, Co, Cu, Zn, Sn, etc.

f) Oligonucleotides: Another useful group of reagents for entrapment includes any suitable RNA, DNA, and labeled or unlabeled oligonucleotides for use as hybridization probes or primers. For instance, in the PCR, any appropriate antisense (reverse) primers and sense (forward) primers can be used including those labeled with any suitable label such as biotin, AP, digoxigenin, sulfur, cyclodextrins, fluorophores, isotopes, and proteins. Also included are members of this group labeled with radioactive nuclides such as $^3$H, $^{14}$C, $^{32}$P, $^{35}$S, and $^{125}$I, among others.

g) Inclusion Compounds: Another group of materials for entrapment is inclusion compounds defined as substances that can assemble to form molecular cavities or have molecular cavities in their structure and are capable of forming a molecular framework around one or more smaller molecules to form a so-called "inclusion complex". Examples are any cyclodextrins (CD's) including α-cyclodextrins, β-cyclodextrins, and δ-cyclodextrins, as well as any dimers, trimers, polymers or derivatives of them. Some examples of cyclodextrins and derivatives are disclosed by Atwood, J. E. D., et al, Eds., "Inclusion Compounds", Vols. 2&3, Academic Press, N.Y. (1984); Bender, M. L., et al, "Cyclodextrin Chemistry", Spring-Verlag, Berlin (1978) and Szejtli, J., "Cyclodextrins and Their Inclusion Complexes", Akademiai Kiado, Budapest, Hungary (1982).

Also included are cavitands, any calixarenes and any cyclophanes. Some examples of calixarenes are disclosed in J. Inclusion Phenom. Molec. Recog. Chem. 7 (1989), by Gutsche, C. D. on pages 61–72 and Shinkai, S., pages 193–201, among others. Some examples of cyclophanes are disclosed by Bukownik, R. R. et al, J. Organ. Chem. 53, (1988), Murakami, Y. et al, J. Chem. Soc. Perkin Trans. I., 1289–1299 (1988), and Reid, W., et al, Tetrahedron 44, No. 11, 3399–3404 (1988), among others.

Also included are assemblies or bundles of helical peptides such as disclosed by Hahn, K. W., et al, Science 248, 1544–1547 (1990). Suitable inclusion compounds for entrapment can also be formed from assemblies or bundles of helical oligonucleotides.

h) Additives, Inhibitors and Chelators: Another useful group of reagents for entrapment is any additives such as surfactants, emulsifiers, antioxidants and stabilizers. Also include are enzyme inhibitors or poisons. Also included are various chelating agents such as ethylenediaminetetraacetic acid (EDTA), ethylene glycol-bis(beta-aminoethyl ether)N,N,N',N'-tetraacetic acid (EGTA), and 2,2',2",2"'-( 1,2-ethanediylidene-tetrakis[thio])tetrakis-acetic acid (ETTA), 1,2-bis(2-aminophenoxy)ethane-N,N,N',N'-tetraacetic acid (BAPTA), among others.

i) Drugs and Antibiotics: Another group of reagents for entrapment is any drugs, vitamins, and antibiotics, such as antimetabolites, sulfonamides, penicillins, cephalosporins, macrolides (i.e. erythromycins), aminoglycosides (i.e. streptomycins, kanamycins, neomycins, gentamicin), chloramphenicols, tetracyclines, rifamycins, actinomycins, as well as any antiviral drugs, anticancer drugs and any derivatives or analogs thereof.

j) Antibodies: Another group of reagents for entrapment is any antibodies, antibody fractions, and especially monoclonal antibodies, including derivatives thereof.

k) Antigens: Another group of reagents for entrapment includes any antigens, such as from human, animal or plant tissues, bacteria, viruses or fungi, or derivatives thereof, as well as antigens synthesized from recombinant DNA methods.

l) Avidins and Streptavidins: Another group of reagents for entrapment is any avidins and streptavidins including derivatives, labeled forms, fractions and recombinant DNA products with avidin properties.

m) Biotins: Another group of reagents for entrapment is any biotins, aminobiotins, photobiotins and any biotinylated proteins, nucleic acids, carbohydrates, or lipids.

n) Labeling substances: Another group of reagents for entrapment is various labeling materials such as any isothiocyanate compounds (FITC, etc.), sulfonyl chloride compounds (4,7-bis(chlorosulfophenyl)-1,10-phenanthroline-2,9-dicarboxylic acid (BCPDA)), N-hydroxysuccinimide esters (N-hydroxysuccinimidobiotin), nucleic acid intercalating dyes (ethidium bromide, psoralens and psoralen derivatives, etc.).

The most preferred intercalating dyes are ethidium bromides, oxazole orange and thiazole orange, especially their dimers (i.e. YOYO and TOTO, Molecular Probes Inc.), trimers and various derivatives. Also included are any suitable dyes and fluorophores conjugated to and/or as inclusion complexes with cyclodextrins and any of the cyclodextrin derivatives disclosed in disclosure documents #247302, Mar. 12, 1990; #244763, Feb. 6, 1990; and #248131, Mar. 19, 1990. These dyes and fluorophores, including YOYO and TOTO, can be subsequently detected by fluorescence, or by a chemiluminescent reaction such as energy transfer from decomposition of certain 1,2 dioxetanes, or peroxyoxylates.

o) Glassy State Mixtures: Another group of reagents for entrapment can include glassy state or candy-like mixtures or solutions. Glassy state or candy-like mixtures are defined as flowable mixtures when warm, that form undercooled, solidified liquids when at room temperature or below. They are composed of high concentrations of glass forming materials in a mixture or solution with water. The water content is generally less than 5%. These mixtures are fluid when heated above their glass transition temperature, but as they are cooled their viscosity rises quickly so that they are solid or semisolid at room temperature. Beads or particles formed by the method of this invention can include mixtures that form a glassy state when cooled. Suitable glass forming substances are carbohydrates, especially the candy-like forms of sucrose and glucose, which are the glassy states of these sugars.

Also preferred are carbohydrate polymers such as Ficoll™ (Pharmacia), various other sugars, cyclodextrins, dextrans, sorbitols and any other suitable materials that will form a glassy state, such as polyvinyl pyrrolidone, polyacrylamide and polyethyleneimine. Some examples are described in U.S. Pat. No. 5,098,893, and in publications by Franks, et al, in; Biopharm. October, pages 38–42 and 55

(1991), and B. Roser, Biopharm. September, pages 47–53 (1991), among others. Suitably, for use in this invention, glassy state mixtures are formulated for entrapment with any other reagents or materials such as those described herein, to provide a glass transition temperature above room temperature and preferably above 30° C.

p) Magnetic Materials: Another group of reagents for entrapment includes magnetic materials. For instance, the addition of suitably coated, ferrous or magnetic particles (Ithakissios, D. S., Clin. Chim. Acta 84(1–2), 69–84, 1978), available from Advanced Magnetics Inc., Cambridge Ma., or Dynal Inc., Great Neck N.Y., can be entrapped with other reagents or incorporated into the entrapping material. When said entrapping material containing magnetic particles is formed into beads by the methods of this invention, the beads have magnetic properties. This is useful for various manipulations such as dispensing, transferring, washing or separating the beads as desired before or during a reaction. Magnetic materials may also serve to increase mixing by providing a means for magnetic stirring of the solution.

q) Coupling or Crosslinking Agents: Another group of reagents for entrapment includes coupling or crosslinking agents. They are defined here as substances that produce or react with active functional groups on the material to be coupled or crosslinked. The appropriate coupling agent is used to activate the functional group or react with it. The coupling agent may provide the linkage between lipids, phospholipids, proteins, carbohydrates or surfactants. Examples of coupling agents are glutaraldehyde, formaldehyde, cyanogen bromide, azides, p-benzoquinone, succinic anhydrides, carbodiimides, maleimides, epichlorohydrin, periodic acid, ethyl chloroformate, dipyridyl disulfide, polyaldehydes, dimethylsuberimidate and other forms of bis(imidoesters), as well as certain heterobifunctional reagents such as m-maleimidobenzoyl-N-hydroxysuccinimide, N-succinimidyl- 3-(2-pyridyldithio)-propionate and N-succinimidyl(4-iodoacetyl)aminobenzoate, among others.

r) Liposomes: Another group of reagents for entrapment includes liposomes. A liposome is a rounded, submicron to many micron-sized, liquid-filled vesicle composed of a lipid bilayer membrane that completely encloses an aqueous space. The lipid bilayer may form a single membrane (unilamellar) or may form several concentric membranes (multilamellar) around the aqueous space. The membrane may be impermeable or semipermeable depending on composition. Liposomes may be synthesized from single chain lipids or surfactant polymers, for example, see: Fendler, J., Science 223, 888–894 (1984); Hammes, G. G. et al, Biochemistry 9, 2555–2563 (1970), among others. They are generally made from mixtures of phospholipids, sterols and various amphiphilic lipids. Any of the water miscible or water soluble reagents for entrapment described herein, can be suitably entrapped inside liposomes which can then be entrapped inside beads made with the instant invention. Reagents can include a variety of proteins, enzymes, substrates, polyamino acids, nucleotides, oligonucleotides, antibodies, antigens and various reaction components.

Also, the liposome membrane composition can be modified through the incorporation of dyes, chromophores and magnetic substances. The properties of temperature stability, fluidity, permeability and surface charge can be altered with sterols, antibiotics and charged or uncharged lipids. The liposomal membrane can also be modified by incorporating into the membrane a wide variety of lipids, proteins, lipoproteins and glycolipids with "activated" functional groups or with specific ligands coupled thereto. For this invention, liposomes with thermal stability in the range of 30–100 degrees centigrade and with a narrow (i.e. 1–5 degrees) transition (melting) temperature range, are preferred. Such thermal stability can be achieved by using natural or synthetic phospholipids, lipids, lecithins, surfactants, etc., that have aliphatic carbon chains of 14 or more carbons.

Many of the methods used for preparing liposomes in the prior art would be useful for preparing the liposomes of this invention. The major modifications would involve the inclusion of the desired substrate(s) or enzyme such as peroxidases, alkaline phosphatases, DNA polymerases, ligases and Q beta replicase, that is preferably heat stable, in the interior of the liposome.

Also, the liposome membrane may be modified by polymerizing or crosslinking certain membrane lipids or dialkyl surfactants containing vinyl, methacrylate, diacetylene, isocyano or styrene coupling groups by chemical means or with ultraviolet light. The degree of crosslinking could be controlled to give the desired stability against premature lysis of, or leakage from the liposome. For more on materials and methods that are applicable to synthesizing polymerized liposomes, see: J. H. Fendler, Science 223, 888–894 (1984); J. Leaver, et al, Biochim. Biophys. Acta. 732,210–218 (1983); "Polymers as Aids in Organic Chemistry", N. K. Mathur, et al, eds., Academic Press, N.Y. (1980);

Another method for stabilizing the liposomes of this invention would be to use the polymerization methods of P. S. Ash, et al, U.S. Pat. No. 4,448,765. To prepare the polymerized liposome of this invention one would include the appropriate amount of aliphatic lipophilic polymers as disclosed by Ash, et al, as part of the vesicle membrane to obtain the desired degree of heat stability.

Waxes and Waxy Polymers

Waxes are defined as water insoluble, organic materials that are solid or semi-solid at room temperature and usually of lower density than water, but can be melted above room temperature to form a dispersible liquid. Preferred waxes include any naturally occurring and synthetic waxes, wax esters, and greases that generally have a melting temperature of 30° C. or more with a range of less than 10° C. and are suitably nonreactive with the reagents or solvents they are exposed to.

Examples of suitable waxes and greases are esters of various long-chain (fatty) alcohols and long-chain acids, preferably where at least one member of the ester has 10 or more carbon atoms, including various unsaturated and branched chain types and also those esters of glycerols and sterols.

Also, certain free alcohols or acids with even or odd numbers of carbons, have wax-like properties of melting temperature and inertness, and would be suitable as heat-releasable waxes. Some examples of saturated fatty acids (and approximate melting point), that can be used in this invention are; capric (31.3° C.), lauric (48° C.), myristic (58° C.) palmitic (63°–64° C.), margaric (59.3° C.), stearic (70.5°–71.5° C.), arachidic (76°–77° C.), behenic (81°–82° C.), tetracosanic (84.5°–85.5° C.), lignoceric (75°–80° C.), cerotic (78° C.), melissic (91° C.), among others. Some examples of unsaturated fatty acids (and approximate melting point), that can be used in this invention are; tiglic (64°–65° C.), hypogaeic (33°–49° C.), gaidic (39° C.), physetoleic (30° C.), elaidic (44°–45° C.), oleic (58°–59° C.), isooleic (44°–45° C.), erudic (33°–34° C.), brassidic (65° C.), isoerudic (54°–56° C.), among others.

Some examples of fatty alcohols (and approximate melting point), that can be used in this invention are; octadecyl (59° C.), carnaubyl (68°–69° C.), ceryl (80° C.), melissyl (88° C.), phytol, among others. Also included are various esters of these and other fatty acids with any suitable fatty alcohols, or sterols such as cholesterol, or glycerols.

Other examples are natural or suitably modified or derivatized waxes such as various plant derived waxes, greases and oils including carnauba wax, cranberry wax, ouricuri wax, candelilla wax, raphia wax, apple, cotton and cactus waxes; waxes and greases produced by bacteria (i.e. cetyl stearate); fungi, protozoa and algae; various invertebrate waxes and greases including insect waxes such as beeswaxes (i.e. triacontyl palmitate, palmatyl palmitate), and Coccus sp. derived waxes (i.e. lac, cochineal and Chinese insect); other animal fats (i.e. triglycerides) and waxes including spermaceti (i.e. cetyl palmitate), lanolin and wool grease. A list of waxes that can be used in this invention is disclosed in "CRC Handbook of Chemistry and Physics", 64th Edition, CRC Press, Inc., Boca Raton, Fla. (1983–1984).

Also included are various derivatives, extracts, and combinations of these materials. For instance, any oil that is suitably hydrogenated, or various new combinations of long-chain fatty acids and long-chain alcohols, usually of 12 or more carbon atoms, to form new esters together and/or in combination with glycerols or sterols. Also included are various waxes, greases and oils produced by recombinant DNA technology.

Other suitable waxes are many natural or synthetic long chain hydrocarbons such as white waxes, paraffins, ceresins, Vaselines, silicon greases and waxes, polychlorinated or polyfluorinated hydrocarbons, polyether waxes and polyester waxes.

Some examples of useful waxes and their chemical formulas are; eicosane ($C_{20}H_{42}$), octacosane ($C_{28}H_{58}$), cetyl palmitate ($C_{32}H_{64}O_2$), and pentaerythritol tetrabehenate ($C_{93}H_{180}O_8$). Some examples of paraffins and approximate melting point (m.p.), that can be used in this invention are; hexacosane (56.4° C.), hentriacosane (59° C.), tacosane (61.4° C.), nonacosane (62.7° C.), triacontane (65.6° C.), hentriacontane (67.6° C.) dotriacontane (69.5° C.), tetratriacontane (72.5° C.), o pentatriacontane (74.4° C.), hexatriacontane (75.7° C.), including others with shorter or longer carbon chains.

One suitable source of paraffin waxes for use in this invention are those from Fluka Chemical Corp., St. Louis, Mo., with m.p.'s of; 44°–46° C., 50°–52° C., 54°–56° C., 58°–60° C., and 68°–74° C.

Waxy polymers are defined as certain types of polymers that have wax-like chemical or physical properties alone or when combined with waxes. Examples of wax-like polymers are polyethylenes and polypropylenes. Examples of polymers that may be combined with waxes to produce waxy polymers are certain gums and rubbers, various kinds of latex, gutta-percha, balata, chicle and various derivatives. Also included are synthetic rubbers such as isoprene polymers, hydrogenated rubber, butadiene polymers, chloroprene polymers and butyl polymers.

Depending on the desired properties, such as melting point, inertness, solubility, buoyancy, etc., any of the waxes or waxy polymers described here can be combined in various proportions to give the desired result. Also, various additives such as surfactants and emulsifiers can be included to increase miscibility with aqueous solutions. Useful waxes or waxy polymers can also include any suitable long-chain hydrocarbon or ester mentioned previously that has been suitably derivatized to give it neutral buoyancy in an aqueous medium. For example, a long-chain hydrocarbon or ester can be suitably chlorinated or fluorinated to make it less buoyant.

Also, under suitable conditions, the wax or waxy polymer can have coloring added to it in the form of a colored or fluorescent dye, preferably any suitable oil or fat soluble dye can be used. Some examples are, Sudan III, Sudan IV, and Sudan Black B. For certain PCR applications, dyes such as Oil Red O, Oil Blue N, Solvent Green, Fat Red, and Sudan Orange can be used, preferably at less than 0.1% wt./vol. concentration.

Gels

A gel is defined as a solid or semisolid mixture at room temperature of any suitable water soluble or water miscible material within a mostly water (greater than 50%), matrix. Entrapped reagents are held within the gel which can subsequently be melted to release the reagents when heated to a critical temperature. Examples of such gels are those made with; agars, agaroses, carageenans, cellulose derivatives, gelatins, and alginates. Also included are suitable combinations of these gels and/or mixed with other polymers such as acrylamides, carbohydrates, styrenes, proteins, gums, latexes and resins.

PREPARATION METHODS

Preparing beads by the methods of this invention generally involves three stages. First, the material that the beads are to be made of is prepared as a fluid material, then the fluid material is made into drops or droplets which are then solidified by exposure to $LN_2$.

Wax Matrix Beads

To prepare wax matrix beads, one or more reagents to be entrapped are mixed directly with the melted wax or waxy polymer. Depending on the application, the reagent can be in granular, powder or liquid form, or previously dissolved or suspended in a suitable liquid. Mixing is done by mechanically homogenizing, stirring, extruding through a small orifice, or sonicating the reagent and molten wax together. If soluble, the reagent may dissolve into the wax or waxy polymer, or the wax may serve as a matrix that contains a suspension of particles, or liquid droplets or a colloid.

In any case, the melted mixture is then extruded or sprayed to form small spherical particles or dispensed as droplets to form larger beads. Several suitable methods can be used, with appropriate modifications.

One method for forming small dispensable bodies is to spray the melted mixture through a heated orifice of appropriate diameter to produce droplets of less than one millimeter diameter. The conditions of temperature and pressure are adjusted to ensure suitable concentration and activity of entrapped reagent upon release. It may be desirable to use a vibrating nozzle similar to that described by R. Nir, et al, Appl. Environ. Microb., 56, 2870–2875 (1990), to produce more uniform microspheres of entrapped reagent. The mixture is sprayed onto the surface of $LN_2$ in a bath or moving stream.

A preferred method of this invention is to dispense the mixture as drops or droplets of one millimeter or more diameter. The dispensing is done by forcing the molten mixture out of an orifice by mechanical pumping or pneumatic pressure. Or, the mixture is allowed to flow by the force of gravity.

Injected LN₂ Beads

Another method for entrapping liquid heat-releasable reagents or reagents for entrapment in a waxy coating is a modification of the "injected bead" method, previously described in U.S. Patent application Ser. No. 936,357. One modification is done during the injection step, where the desired liquid reagent is injected into a drop or droplet of molten wax or waxy polymer while it is still forming at the end of the dispenser tip, just before it is released. The second modification is to let the injected drop fall into a LN₂ bath instead of forming on a solid surface.

The injected LN₂ bead method is readily adapted to automated or semi-automated methods. For instance, a series of dispensing devices for the molten wax or waxy polymer (i.e. heated syringes and tubing), are arranged to dispense a row of several molten droplets simultaneously. The molten droplets are injected with reagent for entrapment before they drop, by a corresponding row of injecting devices (syringes). After injection, the droplets are dropped into the liquid nitrogen.

All of the necessary steps can be automated or semi-automated. For instance, the exact time to inject a forming droplet can be determined when a forming droplet interrupts a beam of light positioned a few millimeters below the dispenser tip, detected with a photodiode. Then, precision drivers such as electronically controlled step motors can be used to turn screws that push a syringe plunger to inject the reagent for entrapment. Other motors can be used to dispense the molten waxy polymer.

Preferably, the heated tube from the waxy polymer dispenser and the tube from the heat-releasable reagent injector lead to the same point. This way, the tip of the injector tube is also heated and is in the proper position to inject as soon as the molten droplet is formed.

The dispenser and injector tips can be fastened together in parallel, or the injector tip can be suitably threaded a short distance inside the end of the dispenser tube to give concentric tubes.

APPLICATIONS

The heat-releasable reagents herein described, can be entrapped into beads prepared by the methods of this invention. The beads can be applied to any of the applications disclosed and referenced in U.S. patent application Ser. No. 936,375, with suitable modification by one skilled in the art. Some examples are:

a) PCR using heat-releasable DNA polymerase or substrates;

b) high temperature reverse transcriptase reactions (RTR), such those reported by A. L. Schaffer, et al, Anal. Biochem. 190, 292–296 (1990) and T. W. Myers, et al, Biochem. 30, 7661–7666 (1991);

c) high temperature nucleic acid sequencing, based on the procedures of F. Sanger, et al, Pr. Natl. Acad. Sci. USA 74, 5463–5467 (1977), S. Tabor, et al, Pr. Natl. Acad. Sci. USA 84, 4767–4771 (1987) and M. A. Innis, et al, Pr. Natl. Acad. Sci. USA 85, 9436–9440 (1988);

d) coupled high temperature RTR and PCR, as reported by T. W. Myers, et al, Biochem. 30, 7661–7666 (1991) and W. T. Tse, et al, Gene 88, 293–296 (1990);

e) booster PCR with or without hot start, based on the methods of G. Ruano, et al, Nucleic Acids Res. 17, 5407 (1989), and G. Ruano, et al, Pr. Natl. Acad. Sci. USA 87, 6296–6300 (1990);

f) nested PCR, described by K. B. Mullis, et al, Methods Enzymol. 155, 335 (1987) and H. A. Erlich et al, Science 252, 1643–1651 (1991), among others;

g) other types of PCR, such as asymmetric PCR, inverse PCR and arbitrarily primed PCR (APPCR), in situ PCR, described by G. J. Nuovo, et al, Amer. J. Pathol. 139, 847–854 and 1239–1244 (1991), inverted PCR (IPCR) as described by S. Takagi, et al, in Biotechniques 13, 176–178 (1992), and heat-soaked PCR (HS-PCR), as described by G. Ruano, et al, in Biotechniques 13, 266–274 (1992);

h) nucleic acid hybridizations, including in situ and "sandwich" hybridization, among others, and include any type of labeled probe, as described by M. S. Urdea, et al, Nucleic Acids Res. 16, 4937–4956 (1988), and; alkaline phosphatase label or peroxidase label detection using the appropriate heat-releasable substrate reagent.

EXEMPLARY APPARATUS FOR MAKING BEADS IN LIQUID NITROGEN

An apparatus for making beads in LN₂ requires two major components. They are, a mixing and dispensing system for the fluid being made into beads, and a LN₂ bath for making and collecting the beads. The mixing can be done in a batch system, where all the materials are combined and mixed in one lot, all at the same temperature, before dispensing into droplets.

Alternatively, mixing can be done in a continuous flow system where the materials are brought together a little at a time in a predetermined ratio and mixed just before dispensing. A continuous flow system has the advantage of permitting materials at differing temperatures to be combined for a short time before dispensing into droplets. Preferably, the materials are in a flowable state where they can be accurately pumped into a mixing chamber. Suitable pumps are piston or peristaltic pumps.

For example, molten wax at 70° to 90° C. can be pumped into a mixing chamber from one container, and an aqueous enzyme reagent held at 30° to 50° C., can be pumped into the same chamber from a separated container. They are combined at a controlled ratio, such as 0.5 to 5% by weight of aqueous reagent to wax, in the mixing chamber. Mixing or homogenizing is done in one chamber, or a series of chambers, by one or more motor driven impellers, or sonicators, or by pressure extrusion through a small orifice. The mixture is continuously dispensed to the dispensing tips to form drops which fall into LN₂ and form beads.

The advantage is that all the enzyme or any other reagent is exposed to the hot wax for the same time interval before being dispensed. This increases the uniformity of reagent activity between beads made at the beginning of a run versus those at the end. This also permits very short heat exposure times for the enzyme or other reagent. A suitable apparatus is diagrammed in FIG. 1.

Mixing and Dispensing

Figure 1:
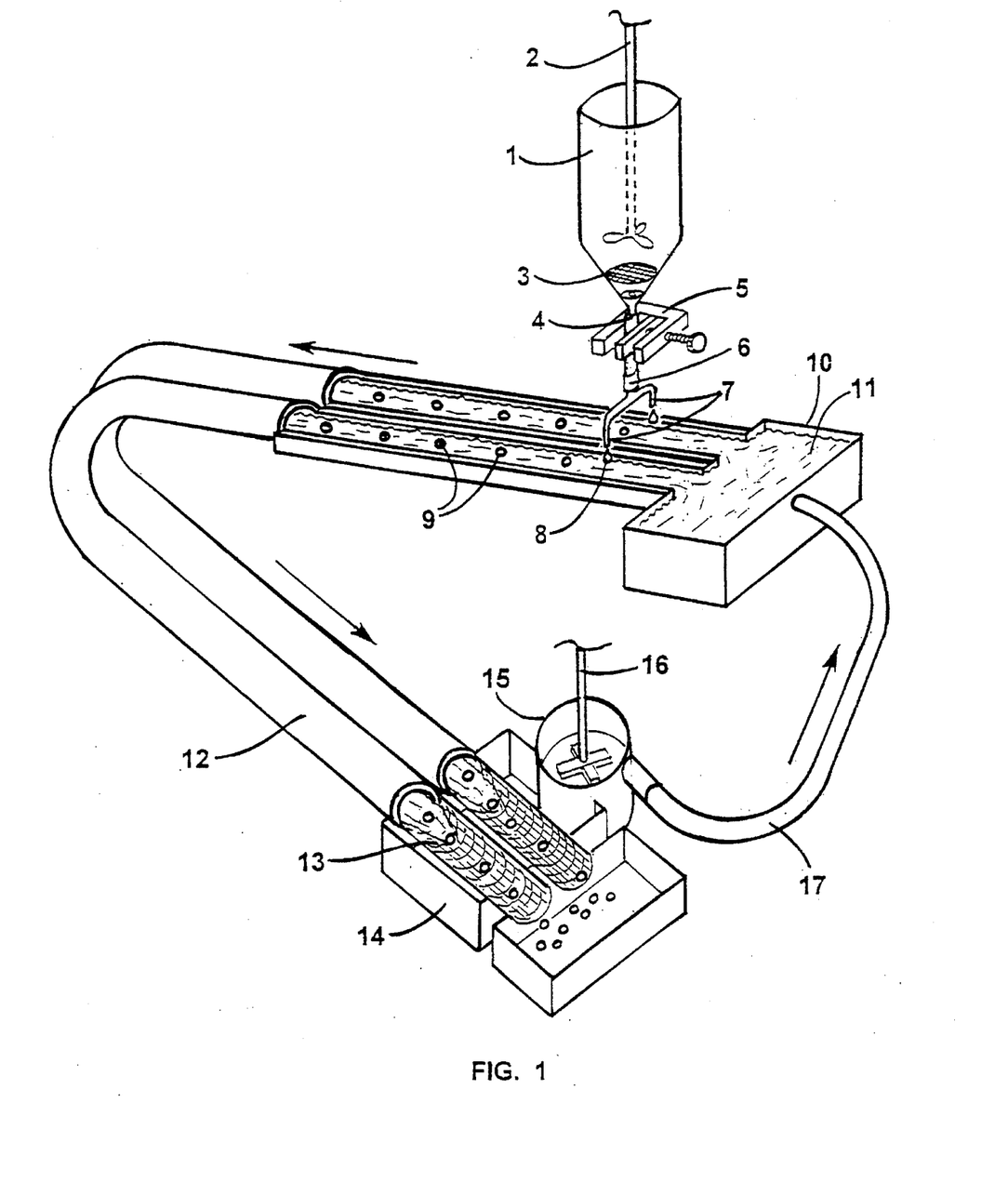
FIG. 1 is a diagram of an apparatus for making beads in liquid nitrogen.

For batch systems, the dispenser consists of a Teflon™, polypropylene or polycarbonate hopper 1, that holds the fluid material for making the beads. The hopper may also include baffles on the sides to facilitate mixing. The top of the hopper is fitted with an adjustable or removable cover with holes in it for a mixing shaft, thermometer, and for adding materials. The fluid is homogenized in the hopper with a suitable S.S. impeller 2, rotated at high enough revolutions per minute (rpm) to homogenize. Or the contents can be homogenized using a sonicator. A fine (about 100 microns), mesh 3, was found necessary to keep large bubbles, generated during mixing, from entering the drain tube.

After homogenizing, the hopper contents are drained or pumped through a connecting tube 4, where the flow rate is controlled with a valve clamp 5. The mixture enters a system of pipes or a manifold 6, that leads to one or more tubular dispensing tips 7. When a molten fluid is being formed into beads, the hopper, manifold and dispensing tips are heated by various means, such as by electric heating coils (not shown in FIG. 1).

A variety of manifold designs are suitable. In this example, the manifold consists of a group of Teflon™ or silicon rubber tubes (about 16 to 18 gauge I.D.), with one end glued as a bundle inside a S.S. pipe. The bundled tubes are cut flush with the end of the steel pipe, which is fitted inside the connecting tube from the drain. The lower, free end of each tube from the manifold is fitted over a dispenser tip or port. The number of tubes bundled in the manifold can be varied to correspond with how many dispenser tips are desired.

The dispenser tips can be of various heat resistant, non-contaminating materials such as Teflon$^{TM}$, silicon or S.S. tubing, or needles, or combinations of these, and of suitable diameter or shape to form the desired size of droplets 8. For instance, using molten wax, we have found the following as typical relationships between dispenser tip and beads produced:

| DISPENSER TIP | EXPER. | MEAN BEAD WEIGHT |
|---|---|---|
| 25 gauge S. S. pointed needle | HB5 | 2.6 mg |
| 20 gauge S. S. blunt needle | HB27 | 6.2 mg  1.6% Coeff. Var. |
| 1/16" ID × 1/8" OD silicon tubing | HB43 | 18.4 mg  2.5% Coeff. Var. |
| 1/16" ID + 1/4" OD concentric silicon | HB58 | 31.7 mg |

The distance between the $LN_2$ surface and the dispenser tip can be between 1/8 inch and 1 inch, or more.

Liquid Nitrogen Bath

The $LN_2$ bath consists of a reservoir 10, that feeds $LN_2$ 11, into a plurality of channels, each one passing under a corresponding dispenser tip. The channels have sufficient depth (e.g. 1/8" or more), of $LN_2$ in them to allow the beads 9, to form from droplets of fluid that are dropped onto the $LN_2$ surface. The $LN_2$ and beads flow (at 4 to 20 inches per second), from each channel into a pipe 12, then over a separation sieve or mesh 13. The beads roll over the mesh into a collection bin while the $LN_2$ is separated by falling through the mesh into a collection trough 14. The $LN_2$ is recirculated when it enters a pump well 15, and is pumped with a centrifugal pump 16, through a return pipe 17, to the reservoir. Another method for collecting the beads is to mechanically sweep or lift them off of the $LN_2$ surface.

Preferably, the $LN_2$ bath is a moving bath where the $LN_2$ carries the beads away from the point of origin and eventually deposits the beads into a collection container. Also, preferably, the beads are separated from the moving $LN_2$ such as by a sieve or screen so that the $LN_2$ is collected and recirculated. The $LN_2$ is recirculated by the use of any suitable pump, preferably a centrifugal pump.

EXAMPLE I

Twelve Port Apparatus for Making Beads In Liquid Nitrogen

In this example, a batch method is used with an apparatus similar to that shown in FIG. 1, to make beads from a molten wax mixture.

Mixing and Dispensing

The hopper consisted of an inverted, one liter polypropylene bottle (#2006-0032, Nalgene Co., Rochester, N.Y.), with a Teflon drain tube (1/4" I.D.) through a rubber stopper glued into the neck with silicon glue (GE280 or GEC54W, General Electric Co., Waterford, N.Y.). The top of the hopper was fitted with a removable polypropylene cover with holes in it to allow passage of a mixing shaft, thermometer, Teflon baffle blade, and a fill hole. The fluid was homogenized in the hopper with a motor driven, three blade S.S. impeller of two inch diameter. The impeller was rotated at over 2000 rpm, with about a five degree angle on the blades.

Over the neck area, about one eighth inch above the drain tube, was glued a two to three inch diameter circle of polypropylene mesh (105 micron, #146436, Spectrum Med. Indust., Los Angeles, Calif.). The drain tube was connected to a lower manifold by a silicon rubber connecting tube, fitted with an adjustable tubing clamp which served as a valve to control flow rate.

The manifold consisted of a group of silicon rubber tubes (about 16 to 18 gauge I.D.), with one end silicon glued as a bundle inside a S.S. pipe (3/8" long X about 3/16" I.D.). In this example, a total of twelve tubes were used in two bundles of six tubes, each fitted at the ends of a polypropylene tee pipe fitting. The tee fitting was inserted into the lower end of the connecting tube. The lower, free end of each tube was fitted over a dispenser tip. In this example the tips were S.S., 16 gauge tubing, about 3/4" long, positioned 1/4 above the channels. The hopper, manifold and dispensing tips are mounted in a S.S. frame that is heated by electric heating coils, controlled manually by a heat regulator (Minitrol, Glas-Col, Terre Haute, Ind.), and monitored with a digital thermometer.

Liquid Nitrogen Bath

The $LN_2$ bath was a moving bath about 1/4 inch deep, consisting of $LN_2$ held in twelve aluminum channels (1/4" wide×3/8" deep×14" long), insulated with Styrofoam. The $LN_2$ was fed into the channels from a common reservoir at their top, from which the $LN_2$ flowed by gravity inside the channels, each passing under one of the dispensing tips, to carry the beads away from their point of origin. The end of each channel directed the flowing $LN_2$ into a pipe (about 1/2" I.D.), sloping downward and carrying the beads and $LN_2$ long enough to allow the wax to cool and solidify but not fracture. Generally, two to five seconds is suitable, with pipes about six feet long. At the end of each pipe is fitted a ten inch long section of plastic sieve or mesh (about 1 to 2 mm mesh size), forming a funnel shaped separation mesh. Below the mesh was positioned a collection trough which emptied into a common pump well, all of which were polystyrene foam insulated. The beads were separated from the $LN_2$ as they left the end of each pipe and rolled over the mesh into a collection bin. As the $LN_2$ left each pipe it fell through the mesh into the trough and was collected in the pump well.

The $LN_2$ was continuously recirculated by pumping it from the pump well, up through a silicon rubber return pipe to the top reservoir feeding the channels. A motor driven, centrifugal pump with a silicon reinforced plastic impeller (about two inches diameter), on an eight inch drive shaft, was used. Pump speed and $LN_2$ flow rate was controlled with a dimmer switch.

General Operation

The hopper was heated to a temperature at or above the melting temperature of the wax being used. With the tubing clamp closed, molten wax was added through a funnel in the fill hole. While mixing the molten wax, the desired reagents were added to the molten wax. $LN_2$ was added to the pump well, and the flow of $LN_2$ was regulated to give a moving bath one eighth inch or more in depth, moving at about six to eighteen inches per second. After sufficient homogenizing, the valve was gradually opened to allow the molten mixture to drip from the dispenser tips into the $LN_2$ bath. A suitable drip rate was one half to five droplets per second, depending on the droplet size and $LN_2$ flow rate.

EXAMPLE II

Wax Beads Containing Magnesium Chloride Reagent

To the apparatus of Example I, with the tubing clamp closed, was added 500 gm of molten p. araffin wax (mp 68°–74° C., Fluka), and heated to about 88° C. While mixing the molten wax, 10 ml of reagent solution was added dropwise over a period of about 10 minutes. The solution contained 5.58 ml water, 3.92 ml of 1.0 M $MgCl_2$ and 0.5 ml 40% Tween 80 in water, to give about 2% aqueous in the wax mixture. The $LN_2$ was turned on and the flow adjusted to about ¼" depth, running at about two feet per second through the channels. The mixture was homogenized for about 15 minutes more, then the valve was opened to allow the mixture to drip from 16 gauge dispenser tips, continuing to homogenize. The dripping mixture was discarded for the first minute by collecting the mixture on layers of paper towel. The towel was then removed and droplets were allowed to fall into the moving $LN_2$ bath. The beads were collected in separate groups based on their time of synthesis, where Group #1 was collected for the first 1 minute of production, Group #2 for the next 6 minutes, Group #3 for the following 3 minutes, and Group #4 collected for the last 1.5 minutes. The peak drip rate was during Group #2, which was about 5 beads per second. The total production time was about 11.5 minutes. The average bead weight was about 13.1 milligrams.

Assay for Released Magnesium

A calmagite stock solution was prepared consisting of 0.016% calmagite in water. A buffer stock solution was prepared consisting of 0.4 M tris buffer, pH 9.0. A 2x indicator solution was prepared fresh by combining the calmagite stock and the buffer stock at a 1:5 ratio.

The Mg concentration was determined by comparing sample absorbance at 515–520 nm to a Mg standard curve. The Mg from each bead was extracted by melting for 1 hour at 80°–90° C. in 1 ml of water. A Mg standard curve was prepared by 0.5 fold serial dilution in water to give concentrations of from 0.02 to about 0.16 mM.

The samples and the standard curve solutions (in duplicate), were diluted ½ with 2X indicator (e.g. combining 1 ml of each), just before reading their absorbance at 515–520 nm on a spectrophotometer (e.g. ELISA plate reader). A linear regression curve was constructed from the Mg standard results and the sample values were calculated from the curve.

| Results | Group No. | | | |
| --- | --- | --- | --- | --- |
| | 1 | 2 | 3 | 4 |
| Mean Bead Weight (Gm) | .01265 | .01339 | .01322 | .01320 |
| Meam mM Mg in 50 µl | 1.69 | 1.67 | 1.68 | 1.72 |
| % Coeff. Var. | 5.7 | 6.9 | 9.3 | 5.0 |
| Beads per Group | 2,648 | 18,006 | 8,896 | 4,000 |
| Total Yield = 33,640 beads. | | | | |

EXAMPLE III

Wax Beads Containing Taq DNA Polymerase

A polypropylene funnel was fitted with a clamped, silicon rubber drain tube, ¹⁄₁₆" ID×⅛" O.D. The funnel and tubing were kept heated with an electric coil to 80°–90° C. To the funnel was added 1.9 gm of molten paraffin wax (mp 68°–74° C.). A stainless steel impeller (8 mm diameter), mounted on a ⅛" O.D. shaft, driven by a Moto-Tool® model 395 (Dremel, Racine Wis.), was suspended in the molten wax.

Below the outlet of the drain tube, a moving bath of liquid nitrogen ($LN_2$), was positioned. The bath of $LN_2$ was held in a Styrofoam channel where it flowed by gravity inside the channel, passing under the drain tube. The $LN_2$ was continuously recirculated by allowing the $LN_2$ to flow into a foam insulated pump well. The $LN_2$ was then pumped back up through a silicon rubber return pipe into a reservoir at the upper end of the channel bath.

While mixing the wax at approximately 15,000 rpm, 0.1 ml of enzyme solution was gradually added. The enzyme solution consisted of 40 µl of aqueous buffer (pH 8.0), containing 200 units of Taq DNA polymerase, 20 mM Tris-HCl, 1 mM dithiothreitol, 0.1 mM EDTA, 0.1 mM KCl, 0.5% Thesit® (Desitin-Werke, W. Germany), 0.2 mg/ml gelatin and 50% (v/v) glycerol (all from Boehringer Mannhelm Corp., Indianapolis, Ind.), combined with 60 µl of water containing 20% Ficoll™.

The mixture was homogenized for 2–3 minutes and then allowed to drip from the drain tube into a flowing stream of liquid nitrogen. The yield was about 60 beads with an average weight of 12.5 milligrams. The dry beads were stored in a freezer at about minus 15° C., and tested at various times.

PCR Test for Release of Active Enzyme

After three months storage, the wax beads containing DNA polymerase were tested in the PCR in a 50 µl reaction volume. A PCR "master mix" was prepared without DNA polymerase, comprising; 5 µl of "10X PCR buffer" which gives 1.5 mM $MgCl_2$ (Boehringer Mannhelm), 10 ng of pBR322 DNA template, $10^{-6}$ M each of pBR322 primers (Bam H I and Eco R I), 0.2 mM each of dATP, dCTP, dGTP, and dTTP (dNTP's), in water (Sigma Chem. Co., St. Louis, Mo.). After dispensing 0.05 ml of master mix into each of four 0.2 ml PCR reaction tubes, five beads were added to each tube.

A control set of four tubes was also prepared with 0.05 ml of the same master mix and 1.5 units of liquid, un-entrapped Taq DNA polymerase added. The samples were denatured for one minute at 96° C., then thermocycled for 40 cycles of; 45 seconds @ 94° C., 45 seconds @ 55° C., and 90 seconds @72° C.

The PCR products were analyzed by a standard method of agarose gel electrophoresis (AGE). The samples were diluted ½ in a loading solution comprising; about 5% Ficoll, SDS and bromophenol blue, and loaded 10 µl into corresponding wells. The AGE was done horizontally using 3% agarose gel in 89 mM tris, 89 mM borate, 2 mM EDTA (TBE) buffer (pH 8), containing 0.5 micrograms/ml of ethidium bromide stain. The gel was run for about 1 hour at 54 volts, 500 milliamps, then subilluminated with U.V. light and photographed through an orange filter with Polaroid instant film.

Results

Figure 2:
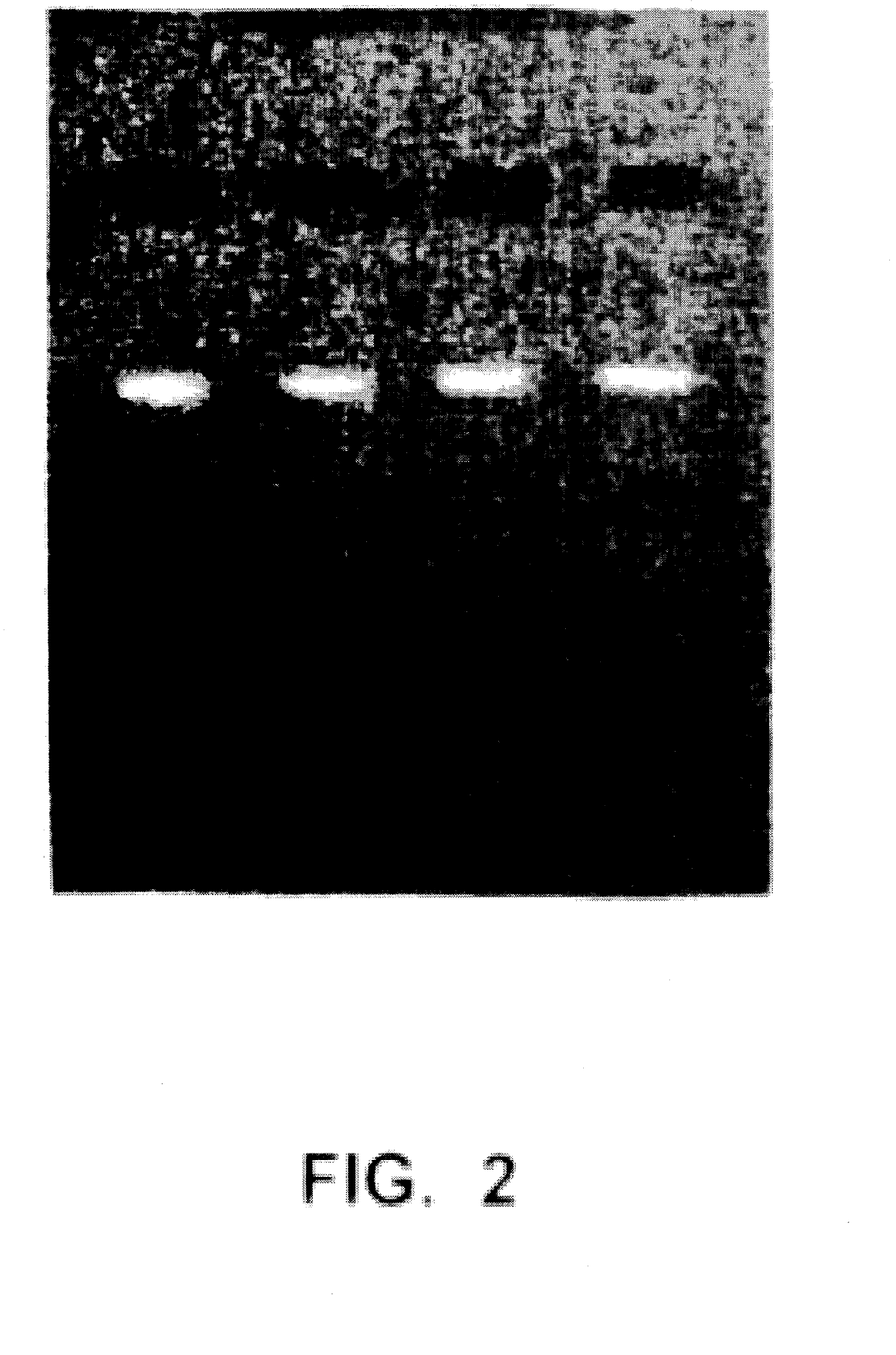
FIG. 2 is a copy of a photograph showing PCR products from enzyme released from wax beads.

As is shown in FIG. 2, DNA product bands can be seen at the top of each lane, which was comparable to the controls (data not shown). These results indicate that the paraffin entrapped Taq DNA polymerase in the beads was released from entrapment during the PCR and successfully amplified the template DNA.

EXAMPLE IV

Preparation of Aqueous Beads in Liquid Nitrogen

A solution was prepared consisting of; 10 ml of water containing 0.1 M $NaH_2PO_4$, pH 6.5, and 1 drop of food color (Schilling). Using a polyethylene transfer pipette, droplets of the solution were dropped into a bath of $LN_2$ in a Styrofoam container, from a height of about 2 inches. Three of the droplets were timed with a digital watch from the moment they hit the $LN_2$ surface until they sank. Four other droplets were allowed to remain on the surface for about 10 seconds, which permitted them to form into frozen beads, and were collected using a polyethylene mesh as a scoop. These beads were kept frozen in a container held a few millimeters above a $LN_2$ bath, and subsequently measured and weighed.

Results

The average time for the aqueous droplets to sink from the surface of the $LN_2$ was 17 seconds.

This method produced very spherical aqueous beads. The four aqueous beads collected were about 4 millimeters in diameter with an average weight of 0.0189 gm, and a standard deviation of 0.000614 gm.

OTHER TYPES OF AQUEOUS BEADS

Example IV demonstrates the versatility of the instant invention in making frozen aqueous beads. Using the methods of the instant invention, many types of aqueous beads can be made.

Frozen Beads

Any of the water soluble or water miscible reagents for entrapment described herein can be included in an aqueous fluid material that is dispensed as drops or droplets into $LN_2$ to form frozen beads. One or more reagents can be included in an aqueous fluid material either as pure reagent or mixed with a suitable stabilizers and carrier substance such as carbohydrates (e.g. glucose, sucrose, Ficoll™, carageenan, agarose, etc.), or proteins (e.g. albumin, gelatin, etc.) or polymers (e.g. polyethylene glycol, acrylamide, styrenes, etc.).

During synthesis, the aqueous fluid material is substituted for the molten wax or waxy polymer in Examples II or III, except that heating the homogenized or mixed fluid may not be needed. Also, if the aqueous fluid material includes only soluble materials, then homogenizing may not be needed once they have been dissolved in the water. In any case, using this invention, frozen, spherical beads can be made containing uniform amounts of the desired reagents that can be stored frozen for future use.

Freeze Dried Beads

One useful application for frozen beads is to produce freeze dried beads or particles. This would require subjecting the frozen beads to well known lyophilizing conditions that includes vacuum drying. The resulting dried beads would have the advantage over conventional dried powders in that each dried bead contains a uniform amount of reagent that can be easily dispensed.

Wax Coated Freeze Dried Beads

Another useful composition is wax or waxy polymer coated freeze dried beads. In this case, the dried beads are coated with a layer of any suitable wax or waxy polymer using various methods such as the "hot melt fluid bed coating press" described by M. J. Jozwiakowski, et al, in Pharmaceutical Res. 7, 1119–1126 (1990). Or, the dried beads can be encapsulated in wax using the method of Lang, et al, U.S. Pat. No. 5,200,236, where the beads are coated by spraying them with molten wax while they are in a fluidized bed. For instance, the dried beads are fluidized in a chamber using an upward flow of warm air, and the wax is melted and sprayed into the chamber as the beads are recirculated and suitably coated.

Gel Beads

The instant invention can also be used to make spherical gel beads. In this case, an aqueous fluid material is prepared that contains any suitable gelling material, as well as any suitable water miscible reagents for entrapment as disclosed herein. Preferably, the fluid containing the gelling material is heated above room temperature to keep it in a flowable state. Using the apparatus of Example I, the aqueous fluid is suitably substituted for molten wax and is formed into drops which fall into $LN_2$ and form spherical gel beads. The resulting gel beads can be stored in a nondrying environment. Alternatively, such gel beads can be freeze dried and coated with wax as described above.

Glassy State Beads

Yet another useful application of the instant invention is for the synthesis of beads containing a glassy state mixture. Any of the water soluble or water miscible reagents for entrapment can be combined with any glass forming materials described herein to form a fluid material. Preferably, the mixture is heated above room temperature to keep it in a flowable state that is dispensed as drops or droplets into $LN_2$ to form beads.

During synthesis, the fluid material is substituted for the molten wax or waxy polymer in Examples II or III, except that homogenizing may not be needed. Alternatively, a glassy state mixture and the desired aqueous reagent mixture can be combined in a continuous flow system as previously described. With a continuous flow system, the glassy mixture can have a high glass transition temperature (e.g. 40° to 90° C.), and can be heated to a much higher temperature than the reagent mixture before they are quickly mixed and dispensed into droplets to form beads in $LN_2$. In any case, using this invention, spherical, glassy state beads can be made containing uniform amounts of the desired reagents that can be stored for future use.

Wax Coated Glassy State Beads

Another useful composition is wax or waxy polymer coated glassy state beads. In this case, the glassy state beads are coated with a layer of any suitable wax or waxy polymer using various methods such as the "hot melt fluid bed coating press" described by M. J. Jozwiakowski, et al, in Pharmaceutical Res. 7, 1119–1126 (1990). Or, the beads can be encapsulated in wax using the method of Lang, et al, U.S. Pat. No. 5,200,236, where the beads are coated by spraying them with molten wax while they are in a fluidized bed. For instance, the glassy beads are fluidized in a chamber using an upward flow of warm air, and the wax is melted and sprayed into the chamber as the beads are recirculated and suitably coated.

While the invention has been described with references to certain specific embodiments, it is understood that changes may be made by one skilled in the art and it would not thereby depart from the spirit and scope of the invention which is limited only by the claims appended hereto.

What is claimed is:

1. A method for producing a wax bead that contains a reagent and is greater than one millimeter in diameter, comprising the steps of:
   a. forming a droplet of molten wax containing said reagent,
   b. cooling said droplet to solidify the molten wax by dropping said droplet onto the surface of liquid nitrogen such that said droplet remains on the surface of the liquid nitrogen until solidified; and
   c. removing the solidified droplet from the surface of the liquid nitrogen before said droplet sinks into the liquid nitrogen and fractures.

2. The method of claim 1 wherein said reagent is a heat resistant enzyme.

3. The method of claim 1 wherein said reagent is selected from the group consisting of nucleotides, deoxynucleoside triphosphates, dideoxynucleoside triphosphates, ribonucleoside triphosphates, and labeled forms thereof.

4. The method of claim 1 wherein said reagent is an enzyme substrate.

5. The method of claim 1 wherein said reagent is metal salt containing a metal selected from the group consisting of Mg, Mn, Fe, Co, Cu, Zn and Sn.

6. The method of claim 1 wherein said reagent is selected from the group consisting of RNA and DNA.

7. The method of claim 1 wherein said reagent is an inclusion compounds capable of forming a molecular framework around one or more smaller molecules.

8. The method of claim 1 wherein said reagent is an antibody.

9. The method of claim 1 wherein said reagent is selected from the group consisting of emulsifier, antioxidant, and chelators.

10. The method of claim 1 wherein said reagent is an intercalating dyes selected from the group consisting of ethidium bromide, oxazole orange, thiazole orange and derivatives thereof.

11. The method of claim 1 wherein said reagent is a carbohydrates.

12. The method of claim 1 wherein said reagent is a magnetic material.

13. The method of claim 1 wherein said reagent is a surfactant.

14. The method of claim 1 wherein said reagent is a stabilizer.

15. The method of claim 1 wherein said reagent is an enzyme inhibitor.

16. The method of claim 1 wherein said reagent is an antigen.

17. The method of claim 1 wherein said reagent is selected from the group consisting of avidin and streptavidin.

* * * * *